US00PP37017P2

(12) United States Plant Patent
Koot

(10) Patent No.: US PP37,017 P2
(45) Date of Patent: Oct. 14, 2025

(54) ***LANTANA* PLANT NAMED 'Dolanhavfumo'**

(50) Latin Name: *Lantana camara*
Varietal Denomination: Dolanhavfumo

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/976,311

(22) Filed: Dec. 10, 2024

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./226, 227
See application file for complete search history.

(56) References Cited

U.S. PATENT DOCUMENTS

PP21,590 P2 * 12/2010 Pan ..... A01H 6/86
Plt./360

OTHER PUBLICATIONS

Rowe Farms. 2020. *Lantana* Havana Full Moon. https://www.facebook.com/GrowwithRowe/posts/lantana-havana-full-moon-lantana-is-a-all-star-for-our-texas-climate-this-fall-l/736762880220673/. 2 pgs. (Year: 2020).*

Dummen Orange 2026 Annual Catalogue. p. 183. Listing for *Lantana* Havana Full Moon. https://na.dummenorange.com/app/pdfcatalogs/detail.web?catalogId=351. 2 pages. (Year: 2025).*

* cited by examiner

*Primary Examiner* — Karen M Redden
(74) *Attorney, Agent, or Firm* — C. Anne Whealy

(57) ABSTRACT

A new and distinct cultivar of *Lantana* plant named 'Dolanhavfumo', characterized by its compact, upright and mounding plant habit; moderately vigorous growth habit and moderate growth rate; freely branching growth habit; dense and bushy plant form; dark green-colored leaves; early and freely flowering habit; long flowering period; flowers that are initially yellow in color becoming white with development; and good garden performance.

1 Drawing Sheet

Botanical designation: *Lantana camara.*
Cultivar denomination: 'DOLANHAVFUMO'.

BACKGROUND OF THE INVENTION

The present invention relates to a new and distinct cultivar of *Lantana* plant, botanically known as *Lantana camara* and hereinafter referred to by the name 'Dolanhavfumo'.

The new *Lantana* plant is a product of a planned breeding program conducted by the Inventor in Rheinberg, Germany. The objective of the breeding program is to create new compact, freely-branching *Lantana* plants with early and freely flowering habit and large attractive flowers.

The new *Lantana* plant originated from a cross-pollination in July 2020 in Rheinberg, Germany of a proprietary selection of *Lantana camara* identified as code number LA19-K0008, not patented, as the female, or seed, parent with a proprietary selection of *Lantana camara* identified as code number LA-0087, not patented, as the male, or pollen, parent. The new *Lantana* plant was discovered and selected by the Inventor as a single flowering plant from within the progeny of the stated cross-pollination in a controlled greenhouse environment in Rheinberg, Germany in April 2021.

Asexual reproduction of the new *Lantana* plant by terminal vegetative cuttings in a controlled greenhouse environment in Rheinberg, Germany since April 2021 has shown that the unique features of this new *Lantana* plant are stable and reproduced true to type in successive generations.

SUMMARY OF THE INVENTION

Plants of the new *Lantana* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dolanhavfumo'. These characteristics in combination distinguish 'Dolanhavfumo' as a new and distinct *Lantana* plant:

1. Compact, upright and mounding plant habit.
2. Moderately vigorous growth habit and moderate growth rate.
3. Freely branching growth habit; dense and bushy plant form.
4. Dark green-colored leaves.
5. Early and freely flowering habit.
6. Long flowering period.
7. Flowers that are initially yellow in color becoming white with development.
8. Good garden performance.

Plants of the new *Lantana* can be compared to plants of the female parent selection. Plants of the new *Lantana* differ primarily from plants of the female parent selection in flower color as flowers of plants of the new *Lantana* are initially yellow in color becoming white with development whereas flowers of plants of the female parent selection are initially yellow in color becoming pink with development. In addition, plants of the new *Lantana* are more compact, more upright and more freely branching than plants of the female parent selection.

Plants of the new *Lantana* can be compared to plants of the male parent selection. Plants of the new *Lantana* differ primarily from plants of the male parent selection in flower color as flowers of plants of the new *Lantana* are initially yellow in color becoming white with development whereas flowers of plants of the male parent selection are initially yellow in color becoming pink with development. In addition, plants of the new *Lantana* are more compact and more upright than plants of the male parent selection.

Plants of the new *Lantana* can be compared to plants of the *Lantana camara* 'Ban Whit', disclosed in U.S. Plant Pat. No. 21,590. In side-by-side comparisons, plants of the new *Lantana* differ from plants of 'Ban Whit' in the following characteristics:

1. Plants of the new *Lantana* are larger and more upright than plants of 'Ban Whit'.
2. Plants of the new *Lantana* are more freely branching and denser than plants of 'Ban Whit'.
3. Plants of the new *Lantana* have larger leaves than plants of 'Ban Whit'.
4. Plants of the new *Lantana* have broader inflorescences than plants of 'Ban Whit'.

BRIEF DESCRIPTION OF THE PHOTOGRAPH

The accompanying colored photograph illustrates the overall appearance of the new *Lantana* plant showing the colors as true as it is reasonably possible to obtain in colored reproductions of this type. Colors in the photograph may differ slightly from the color values cited in the detailed botanical description which accurately describe the colors of the new *Lantana* plant.

The photograph is a side perspective view of a typical flowering plant of 'Dolanhavfumo' grown in a container.

DETAILED BOTANICAL DESCRIPTION

The aforementioned photograph and following observations and measurements describe plants grown during the spring and summer in 22-cm containers in a glass-covered greenhouse in Rheinberg, Germany and under commercial practices typical of commercial *Lantana* production. During the production of the plants, day and night temperatures averaged 18° C. and light levels ranged from 1,500 to 4,500 lux. Plants were twelve weeks old when the photograph and the detailed description were taken. In the following description, color references are made to The Royal Horticultural Society Colour Chart, Fifth Edition, except where general terms of ordinary dictionary significance are used.

Botanical classification: *Lantana camara* 'Dolanhavfumo'.

Parentage:

*Female, or seed, parent*.—Proprietary selection of *Lantana camara* identified as code number LA19-K0008, not patented.

*Male, or pollen, parent*.—Proprietary selection of *Lantana camara* identified as code number LA-0087, not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 158A in color, actual color of the roots is dependent on substrate composition, water quality, fertilizers, substrate temperature and age of roots.

*Rooting habit*.—Freely branching; dense.

Plant description:

*Plant and growth habit*.—Compact, upright and mounding plant habit; moderately vigorous growth habit and moderate growth rate; freely branching habit, dense and bushy plant form.

*Plant height, soil level to top of foliar plane*.—About 28 cm.

*Plant height, soil level to top of floral plane*.—About 28 cm.

*Plant diameter*.—About 51 cm.

Lateral branch description:

*Branching habit*.—Freely branching habit with about seven primary lateral branches each with about 14 secondary lateral branches developing per plant.

*Length*.—About 31 cm.

*Diameter*.—About 6 mm.

*Internode length*.—About 2.7 cm.

*Strength*.—Strong.

*Texture and luster*.—Pubescent; semi-glossy; longitudinally ridged.

*Color, developing stems*.—Close to 144A.

*Color, developed stems*.—Close to 144A, 199A and 199B.

Leaf description:

*Arrangement*.—Opposite, simple.

*Length*.—About 8.7 cm.

*Width*.—About 4.5 cm.

*Shape*.—Ovate.

*Apex*.—Acute.

*Base*.—Rounded.

*Margin*.—Serrate; sinuses are medium in depth and divergent.

*Texture and luster, upper surface*.—Coarse pubescence; semi-glossy.

*Texture and luster, lower surface*.—Coarse pubescence; matte.

*Venation pattern*.—Pinnate, reticulate.

*Color*.—Developing leaves, upper surface: Close to N137D. Developing leaves, lower surface: Close to 137B. Fully expanded leaves, upper surface: Close to N189A; venation, close to 137C. Fully expanded leaves, lower surface: Close to 189A; venation, close to 139D.

*Petioles*.—Length: About 1.5 cm. Diameter: About 2.2 mm. Strength: Moderately strong. Texture and luster: Smooth, glabrous; matte. Color, upper surface: Close to 137C. Color, lower surface: Close to 139D.

Flower description:

*Flower arrangement and flowering habit*.—Solitary salverform flowers arranged in terminal and axillary hemispherical umbels; flowers face mostly upward or outward depending on their position on the umbel; freely flowering habit with about 26 flowers per inflorescence and numerous inflorescences continuously developing per plant during the flowering season.

*Natural flowering season*.—Early flowering habit, plants begin flowering about eight weeks after planting rooted cuttings; long flowering period, plants of the new *Lantana* flower continuously from the spring into the autumn in Germany.

*Flower longevity on the plant*.—Individual flowers last about seven days; flowers persistent.

*Fragrance*.—None detected.

*Inflorescence height*.—About 2 cm.

*Inflorescence diameter*.—About 4.8 cm.

*Flower buds*.—Length: About 5 mm. Diameter: About 2 mm. Shape: Oval to tubular. Texture and luster: Rippled, glabrous; matte. Color: Close to 154C.

*Flowers*.—Appearance: Flared trumpet, salverform; corolla fused, five-parted. Diameter: About 11.8 mm by 14.8 mm. Depth (height): About 2.2 cm. Throat diameter: About 1.5 mm. Tube length: About 1.3 cm. Tube diameter: About 2 mm.

*Corolla*.—Arrangement: Single whorl of five fused petals. Petal lobe length: About 9.2 mm. Petal lobe width: About 4 mm to 8 mm. Petal lobe shape: Obovate. Petal lobe apex: Rounded. Petal margin: Entire; slightly undulate. Petal texture and luster, upper and lower surfaces: Smooth, glabrous; matte. Throat texture and luster: Smooth, glabrous; matte. Tube texture and luster: Smooth, glabrous; matte. Color: When opening, upper surface: Close to 7D and 14A. When opening, lower surface: Close to 11B. Fully opened, upper surface: Close to 1D, 2D and 12A and becoming closer to NN155C with development; venation, similar to lamina color; color does not change with subsequent development. Fully opened, lower surface: Close to 155A and becoming closer to NN155C; venation, similar to lamina color; color does not change with subsequent development. Throat (inside): Close to 12A and becoming closer to NN155C with development; venation, similar to lamina color. Tube (outside): Close to 1C and becoming closer to 155C with development; venation, similar to lamina color.

*Calyx*.—Appearance: Tubular calyx with five fused sepals. Sepal length: About 9.2 mm. Sepal diameter: About 2 mm. Sepal shape: Ligulate. Sepal apex: Acute. Sepal margin: Entire. Sepal texture and luster, upper surface: Coarse pubescence; semi-glossy. Sepal texture and luster, lower surface: Coarse pubescence; matte. Sepal color, upper and lower surfaces: Close to 138A and 137A.

*Peduncles*.—Length: About 5.5 cm. Diameter: About 3 mm. Strength: Strong. Aspect: Mostly upright. Texture and luster: Pubescent; semi-glossy. Color: Close to 138A.

*Pedicels*.—Length: About 1 mm. Diameter: About 1 mm. Strength: Strong. Aspect: Mostly upright. Texture and luster: Smooth, glabrous; semi-glossy. Color: Close to 138A.

*Reproductive organs*.—Stamens: Quantity and arrangement: Four per flower, adnate to floral tube. Filament length: About 1 mm. Filament color: Close to 155A. Anther size: About 0.3 mm by 1 mm. Anther shape: Oval. Anther color: Close to 7A. Pollen amount: Moderate. Pollen color: Close to 7A. Pistils: Quantity: One per flower. Pistil length: About 5.1 mm. Style length: About 2.7 mm. Style color: Close to 157D. Stigma diameter: About 0.5 mm. Stigma shape: Round. Stigma color: Close to 138B. Ovary color: Close to 144A. Fruits: Quantity produced per plant: About five during the flowering season. Length: About 5 mm. Diameter: About 7 mm. Texture: Rough. Color: Close to 202A. Seeds: Quantity per flower: About one to five. Length: About 4 mm. Diameter: About 5 mm. Texture: Smooth, glabrous. Color: Close to 200D.

Garden performance: Plants of the new *Lantana* have been observed to have good garden performance and to tolerate wind, rain and to be suitable for USDA Hardiness Zones 11 and 12.

Pathogen & pest tolerance: To date, plants of the new *Lantana* have not been observed to be tolerant to pathogens and pests common to *Lantana* plants.

It is claimed:

1. A new and distinct *Lantana* plant named 'Dolanhavfumo' as herein illustrated and described.

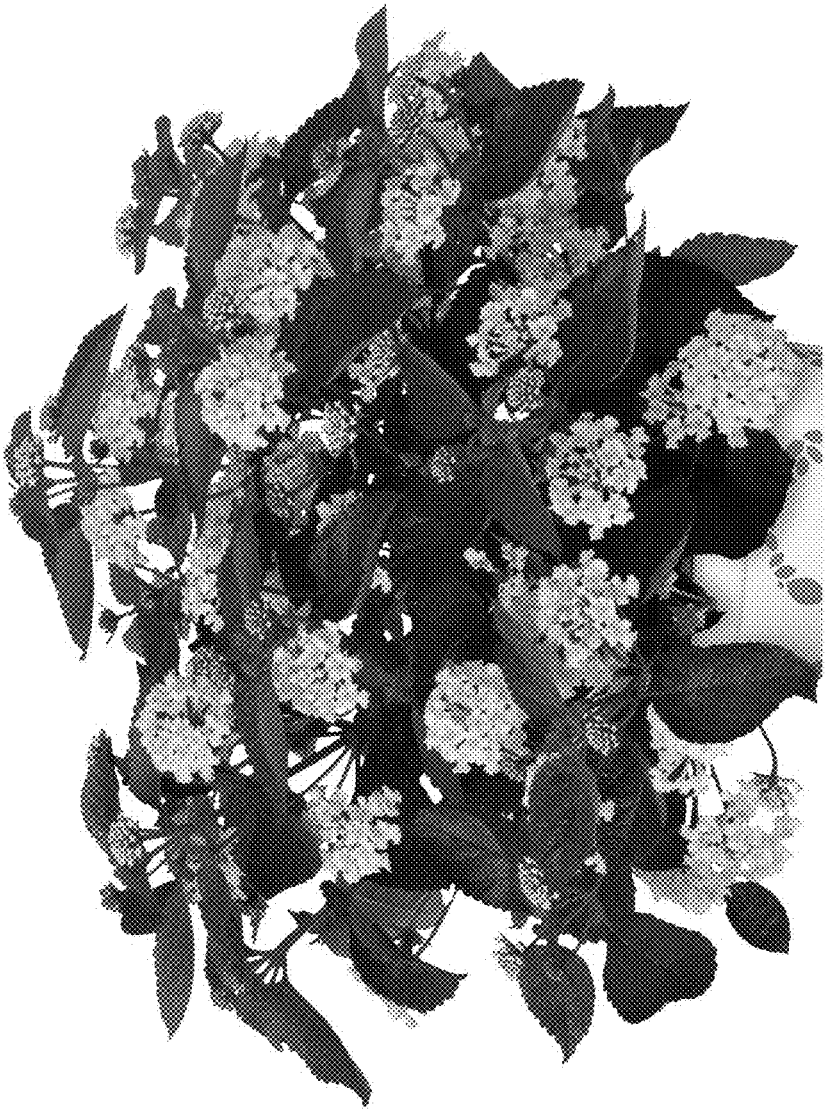

* * * * *